United States Patent
Hirai et al.

(10) Patent No.: US 9,892,526 B2
(45) Date of Patent: Feb. 13, 2018

(54) RADIOTHERAPY APPARATUS AND RADIOTHERAPY METHOD

(71) Applicants: Kabushiki Kaisha Toshiba, Minato-Ku (JP); National Institutes for Quantum and Radiological Science and Technology, Chiba-shi (JP)

(72) Inventors: Ryusuke Hirai, Shinagawa (JP); Yukinobu Sakata, Kawasaki (JP); Yasunori Taguchi, Kawasaki (JP); Tomoyuki Takeguchi, Kawasaki (JP); Shinichiro Mori, Chiba (JP); Fumi Maruyama, Miura (JP)

(73) Assignees: KABUSHIKI KAISHA TOSHIBA, Minato-ku (JP); National Institutes for Quantum and Radiological Science and Technology, Chiba-shi (JP)

( * ) Notice: Subject to any disclaimer, the term of this patent is extended or adjusted under 35 U.S.C. 154(b) by 21 days.

(21) Appl. No.: 15/232,914

(22) Filed: Aug. 10, 2016

(65) Prior Publication Data
US 2017/0046856 A1 Feb. 16, 2017

(30) Foreign Application Priority Data
Aug. 11, 2015 (JP) ................................. 2015-158790

(51) Int. Cl.
*G06K 9/00* (2006.01)
*G06T 11/00* (2006.01)
(Continued)

(52) U.S. Cl.
CPC .............. *G06T 11/003* (2013.01); *A61B 6/00* (2013.01); *A61N 5/1049* (2013.01);
(Continued)

(58) Field of Classification Search
CPC .......... A61N 2005/1061; A61N 5/1049; A61N 5/1075; A61N 2005/1055; A61B 6/00
(Continued)

(56) References Cited

U.S. PATENT DOCUMENTS 9,314,160 B2* 4/2016 Adler, Jr. .............. A61B 5/0033
2016/0256714 A1* 9/2016 Field .................... A61N 5/1075

* cited by examiner

*Primary Examiner* — Charlotte M Baker
(74) *Attorney, Agent, or Firm* — Oblon, McClelland, Maier & Neustadt, L.L.P.

(57) ABSTRACT

A radiotherapy apparatus includes an receiver receiving a first projection image of a calibration object under X-ray imaging; a storing portion storing an ideal projection image of the calibration object, the ideal projection image generated based on design information of an X-ray imaging structure, positional information of the calibration object, and volume data of the calibration object; a calculator calculating a transformation parameter for transforming the first projection image into an ideal projection image; a transformed image generator generating a transformed projection image of the patient by transforming a second projection image of a patient obtained under X-ray imaging with the transformation parameter; a reconstructed image generator generating a reconstructed projection image based on volume data of the patient, positional information of the patient, and the design information; and a matching image generator generating a matching reference image used for matching between the transformed projection image and the reconstructed projection image.

4 Claims, 4 Drawing Sheets

(51) Int. Cl.
*A61N 5/10* (2006.01)
*A61B 6/00* (2006.01)
*G06T 7/33* (2017.01)

(52) U.S. Cl.
CPC ............ *A61N 5/1075* (2013.01); *G06T 7/344* (2017.01); *A61N 2005/1061* (2013.01); *A61N 2005/1076* (2013.01); *G06T 2207/10116* (2013.01); *G06T 2207/30096* (2013.01)

(58) Field of Classification Search
USPC ....................................................... 382/132
See application file for complete search history.

$$\lambda \begin{pmatrix} u \\ v \\ 1 \end{pmatrix} = p \begin{pmatrix} X \\ Y \\ Z \\ 1 \end{pmatrix} \quad (1)$$

$$P_i = P_0 exp\{-\oint \mu(l,P)dl\} \quad (2)$$

$$I'(u',v') = I(u,v) \quad (3)$$

$$\begin{cases} u' = f_x(u,v) \\ v' = f_y(u,v) \end{cases} \quad (4)$$

$$\begin{cases} \lambda \begin{pmatrix} u \\ v \\ 1 \end{pmatrix} = p \begin{pmatrix} X \\ Y \\ Z \\ 1 \end{pmatrix} \\ \lambda' \begin{pmatrix} u' \\ v' \\ 1 \end{pmatrix} = p' \begin{pmatrix} X \\ Y \\ Z \\ 1 \end{pmatrix} \end{cases} \quad (5)$$

$$\lambda' \begin{pmatrix} u' \\ v' \\ 1 \end{pmatrix} = H(\lambda) \begin{pmatrix} u \\ v \\ 1 \end{pmatrix} \quad (6)$$

$$\lambda' \begin{pmatrix} u_d' \\ v_d' \\ 1 \end{pmatrix} = H(\lambda_d) \begin{pmatrix} u_d \\ v_d \\ 1 \end{pmatrix} \quad (7)$$

RADIOTHERAPY APPARATUS AND RADIOTHERAPY METHOD

CROSS-REFERENCE TO RELATED APPLICATIONS

This application claims the benefit of priority of Japanese Patent Application No. 2015-158790, filed on Aug. 11, 2015, the entire contents of which are incorporated herein by reference.

FIELD

Embodiments described herein relate generally to a radiotherapy technology to treat a lesion by irradiating the lesion with a beam.

BACKGROUND

Radiotherapy is a therapeutic technique of destroying a lesion by irradiating the lesion with a therapeutic beam. Thus, unless a therapeutic beam is precisely radiated at the position of the target lesion, there is a possibility that normal tissues around the target lesion are also destroyed.

For this reason, first, CT (computed tomography) imaging is performed on a patient in advance of irradiation of a therapeutic beam in many cases, in order to acquire volume data inside the patient's body and three-dimensionally identify a position of a lesion.

Next, a treatment plan including an irradiation direction and irradiation intensity of a therapeutic beam is determined on the basis of the volume data inside the patient's body so that normal tissues are subjected to as little irradiation as possible.

Then, in an irradiation phase of a therapeutic beam, a bed on which a patient lying is moved and adjusted so that a therapeutic beam is precisely aimed at the lesion position identified with the patient volume data, the lesion position acquired through the treatment plan.

And then, immediately before irradiation of a therapeutic beam, confirmation is performed as to whether the aiming point of a therapeutic beam actually matches or not with the identified lesion position of the patient lying on the bed.

Confirmation of matching between the aiming point of a therapeutic beam and the lesion position is performed on the basis of matching processing between an X-ray projection image obtained by imaging the patient lying on a bed with the use of an X-ray imaging unit permanently mounted on a radiotherapy apparatus and a DRR (Digitally Reconstructed Radiograph) reconstructed as a projection image from the volume data used for the treatment plan. Specifically, confirmation of matching between the aiming point of a therapeutic beam and the lesion position is performed by determining whether the lesion positions of both match each other or not in the above-described matching processing.

Although many methods such as automation are proposed for the above confirmation, ultimately, an inspection engineer visually checks whether the aiming point of a therapeutic beam matches or not with the actual lesion position.

In some cases, irradiation of a therapeutic beam on a patient in radiotherapy is performed for several times to some dozen times over plural days changing a posture of the patient on a bed. Thus, confirmation of matching between an aiming point of a therapeutic beam and a lesion position is performed each time of irradiating the patient with a therapeutic beam, e.g., each day of performing irradiation.

Meanwhile, a position, an angle, and other imaging conditions of an X-ray imaging unit permanently mounted on a radiotherapy apparatus are changing with time. Thus, there is a problem that an X-ray projection image of a patient imaged by an X-ray imaging unit does not necessarily match a projection image reconstructed from volume data each time.

[Patent Document 1] Japanese Unexamined Patent Application Publication No. 2014-171763

BRIEF DESCRIPTION OF THE DRAWINGS

FIG. 2 illustrates formulas by which transformation parameters are derived according to principle of the present embodiment;

DETAILED DESCRIPTION

Hereinafter, embodiments of the present invention will be described with reference to the accompanying drawings.

Figure 1:
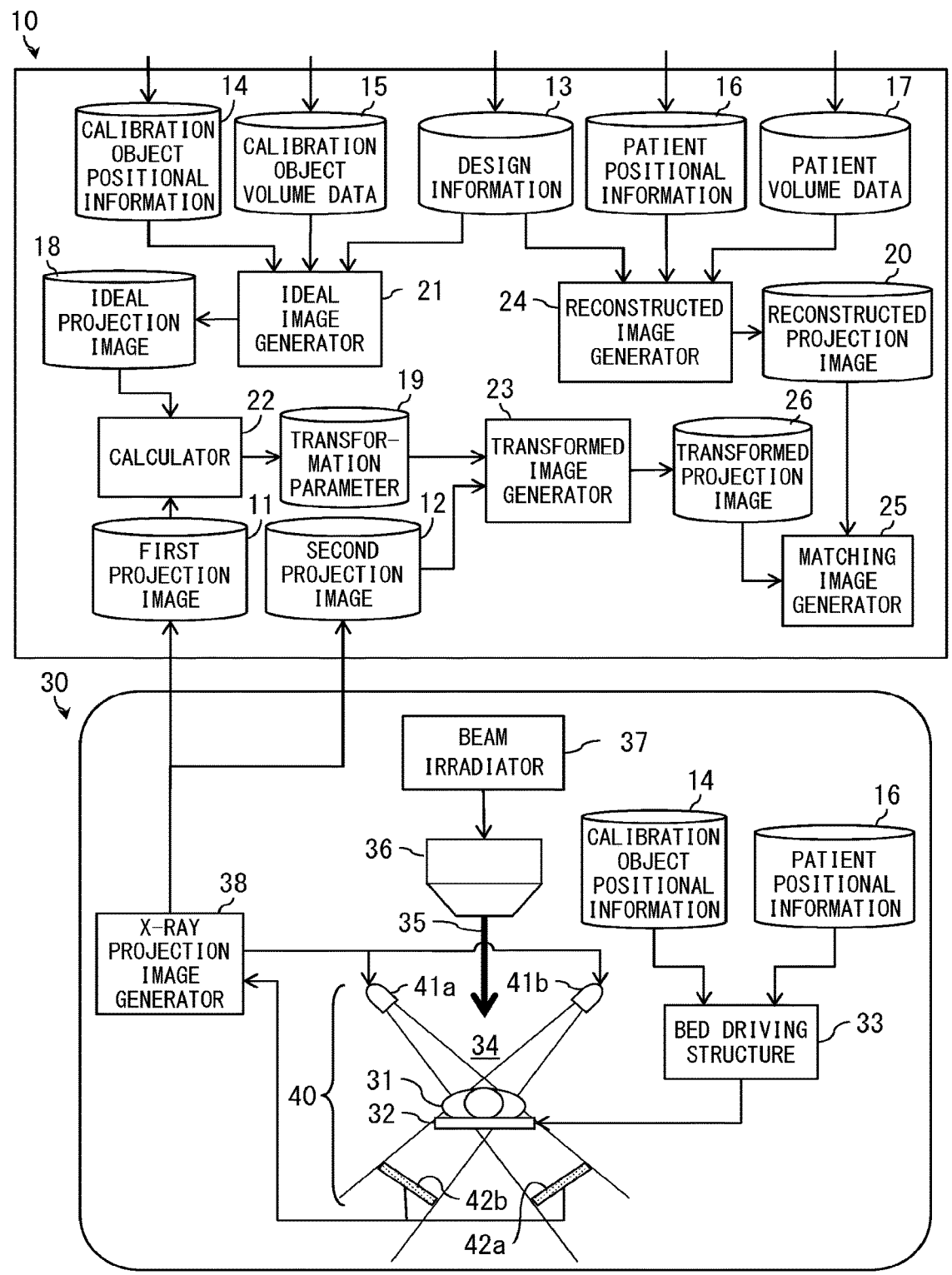
FIG. 1 is a block diagram illustrating configuration of a radiotherapy apparatus according to the present embodiment.

As shown in FIG. 1, a radiotherapy apparatus according to the present embodiment includes a radioactive-ray irradiation system 30 and a control computer 10 configured to control this radioactive-ray irradiation system 30.

The control computer 10 of the radiotherapy apparatus includes a first receiver (not shown), a storing portion (not shown), a calculator 22, a second receiver (not shown), a transformed image generator 23, a reconstructed image generator 24, and a matching image generator 25.

The first receiver receives a first projection image 11 of a calibration object loaded on a bed 32 which has been moved to an irradiation region 34 of a therapeutic beam 35 of treating a patient 31, and the first projection image 11 is obtained by performing X-ray imaging on the calibration object. The storing portion stores an ideal projection image 18 of the calibration object, the ideal projection image 18 generated on the basis of (a) design information 13 of an X-ray imaging structure 40 configured to perform X-ray imaging, (b) calibration object positional information 14 in the irradiation region 34, and (c) volume data 15 of the calibration object. The calculator 22 calculates at least one transformation parameter 19 by which the first projection image 11 is transformed into the ideal projection image 18. The second receiver receives a second projection image 12 obtained by performing X-ray imaging on the patient 31 lying on the bed 32 which has been moved to the irradiation region 34. The transformed image generator 23 generates a transformed projection image 26 of the patient 31 which is a resultant image of transforming the second projection image 12 based on the transformation parameter 19. The reconstructed image generator 24 generates a reconstructed projection image 20 based on volume data 17 obtained by three-dimensionally imaging inside of the patient's body, positional information 16 of the patient 31 in the irradiation region 34, and the design information 13. The matching image generator 25 generates a matching reference image by which matching processing between the transformed projection image 26 and the reconstructed projection image 20 is performed.

The radioactive-ray irradiation system 30 of the radiotherapy apparatus includes a beam irradiator 37, a bed driving structure 33, an X-ray imaging structure 40, and an X-ray projection image generator 38. The beam irradiator 37 outputs a therapeutic beam 35 from a muzzle 36. The bed driving structure 33 controls a position of the bed 32 by moving the bed 32 within the irradiation region 34 based on the calibration object positional information 14 and the positional information 16 of the patient 31. The X-ray imaging structure 40 includes X-ray generators 41a and 41b and X-ray receivers 42a and 42b. Hereinafter, the X-ray generators 41a and 41b are collectively referred to as the X-ray generator 41, arbitrarily. Similarly, the X-ray receivers 42a and 42b are collectively referred to as the X-ray receiver 42, arbitrarily. The X-ray projection image generator 38 outputs the first projection image 11 of the calibration object and the second projection image 12 of the patient 31 imaged by controlling the X-ray imaging structure 40.

Here, a therapeutic beam 35 is a beam of radioactive rays which are radiated on a diseased part such as cancer and kill cells of the diseased part. As such radioactive rays, X-rays, γ-rays, electron rays, proton rays, neutron rays, and a heavy particle beam are included.

Dose of radioactive rays on normal tissues around a diseased part can be minimized by rotating the muzzle 36 of a therapeutic beam about the body axis of the patient 31 so that the diseased part is irradiated with a therapeutic beam 35 from multiple directions. Additionally or alternatively, dose of radioactive rays on normal tissues around a diseased part can be minimized by fixing the muzzle 36 and changing a position of the patient 31 so that the diseased part is irradiated from multiple directions.

In a phase before being treated with the radioactive-ray irradiation system 30, CT (Computed Tomography) imaging is performed on the patient 31 in the same posture as the posture at the time of being irradiated with a therapeutic beam 35 so as to acquire the patient volume data 17 indicative of an intracorporeal stereoscopic image including the diseased part and determine a treatment plan.

In a phase of determining a treatment plan, specialized staff members discuss irradiation conditions of radioactive-rays to be radiated on the diseased part such as dose, an irradiation angle, an irradiation range, and number of irradiation treatments, and then the positional information 16 of the patient 31 to be set in the irradiation region 34 is determined.

Since positional relationship between the bed 32 and the patient 31 is fixed by, e.g., a fixing member, the bed driving structure 33 can control a position of the bed 32 based on the positional information 16 of the patient 31 so as to move the bed 32 to a position where the aiming point of a therapeutic beam 35 matches the diseased part of patient 31.

The design information 13 of the X-ray imaging structure 40 is design information indicative of arrangement of each of the X-ray generators 41a and 41b and the X-ray receivers 42a and 42b such as a mechanical position and an angle in a spatial coordinate system.

Data of the X-ray imaging structure 40 (i.e., the X-ray generator 41 and the X-ray receiver 42) and the volume data 17 are set to a common spatial coordinate system. Thus, it is ideal that arrangement of the X-ray imaging structure 40 in the common spatial coordinate system matches its arrangement in a real space and arrangement of the volume data 17 in the common spatial coordinate system matches its arrangement in a real space.

When the above-described ideal condition is satisfied, the reconstructed projection image 20 outputted from the reconstructed image generator 24 matches the second projection image 12 (i.e., a projection image of the patient 31) outputted from the X-ray projection image generator 38.

However, in fact, conditions of the permanently installed X-ray imaging structure 40 are changing with time, and matching between the second projection image 12 of the patient 31 imaged by the X-ray imaging structure 40 and the reconstructed projection image 20 is not ensured.

Meanwhile, the above-described calibration object is generally referred to as a QA (Quality Assurance) phantom in medical practice. Various types of test objects such as an object model for apparatus calibration, an object simulating a malignant tumor and/or an intracorporal tissue are disposed in the calibration object, and the calibration object is used for acquiring apparatus conditions such as dose and image quality. Since the calibration object is artificially formed as described above, the volume data 15 indicative of the internal structure of the calibration object is generated in advance.

Calibration of the X-ray imaging structure 40 using this calibration object is performed as a daily check of the radiotherapy apparatus.

The calibration object positional information 14 is information on preliminarily determined spatial coordinates of the calibration object disposed in the irradiation region 34 for performing the above-described calibration. When the calibration object is disposed at a predetermined position on the bed 32 and the bed driving structure 33 is caused to operate based on the calibration object positional information 14, the calibration object is automatically disposed at the position of the irradiation region 34 having been set as one of the irradiation conditions.

After moving the calibration object to the irradiation region 34 based on the positional information 14 as described above, the control computer 10 receives the first projection image 11 of the calibration object by causing the X-ray imaging structure 40 to perform x-ray imaging on the calibration object.

An ideal image generator 21 generates the ideal projection image 18 of the calibration object based on the design information 13 of the X-ray imaging structure 40, the calibration object positional information 14, and the volume data 15 of the calibration object, causes the storing portion of the control computer 10 to store the generated ideal projection image 18.

Since conditions of the permanently installed X-ray imaging structure 40 changed with time as described above, a position of the X-ray imaging structure 40 in a real space does not match the position indicated by its design information 13 in some cases. Thus, depending on the gap between the design information 13 and the conditions of the X-ray imaging structure 40 in a real space, the first projection image 11 of the calibration object deviates from its ideal projection image 18.

The calculator 22 calculates plural transformation parameters 19 by which the first projection image 11 of the calibration object is transformed into the ideal projection image 18. The transformation parameters 19 never change as long as the conditions of the X-ray imaging structure 40 in a real space are constant, and have an effect of eliminating the gap between the second projection image 12 of the patient 31 and the reconstructed projection image 20 of the patient volume data 17.

The transformed image generator 23 generates the transformed projection image 26 which is a resultant image of transforming the second projection image 12 based on the transformation parameters 19.

The matching image generator 25 generates a matching reference image by which matching processing between the transformed projection image 26 of the patient 31 and the reconstructed projection image 20 is performed. When the transformed projection image 26 of the patient 31 and the reconstructed projection image 20 do not match each other, it is concerned that the aiming point of a therapeutic beam 35 deviates from the diseased part of the patient 31 for some reasons such as abnormality in the bed driving structure 33. As another possible reason for this, the patient 31 may have been moved from a predetermined position.

In such a case, the bed driving structure 33 adjusts the bed position again until the transformed projection image 26 of the patient 31 and the reconstructed projection image 20 matches each other, and then the therapeutic beam 35 is radiated from the muzzle 36.

Incidentally, determination as to whether the transformed projection image 26 of the patient 31 matches or not with the reconstructed projection image 20 is automatically performed by image processing of a processor in some cases and is visually performed by a medical staff member in some cases.

Hereinafter, principle of deriving the transformation parameters 19 will be described according to FIG. 2, referring to FIG. 1 as required.

In radiotherapy, it is required to align a three-dimensional position of the patient 31. If a three-dimensional position inside the patient 31 is determined on the basis of only one projection image, the determined position includes indefiniteness. Thus, two projection images are obtained by the X-ray imaging structure 40 equipped with one pair of the X-ray generators 41a and 41b and one pair of the X-ray receivers 42a and 42b.

In a three-dimensional space where the X-ray imaging structure 40 is installed, a coordinate system consisting of an X-axis, a Y-axis, and a Z-axis whose origin is an appropriate point is set as an apparatus coordinate system.

When the respective coordinate positions of the X-ray generators 41a and 41b and the X-ray receivers 42a and 42b in the apparatus coordinate system are specified, a projection matrix p like the formula (1) in FIG. 2 can be determined. In the formula (1), u and v indicate a position (u, v) of each of plural detection elements constituting the X-ray receiver 42. Additionally, X, Y, and Z in the formula (1) indicate coordinates (X, Y, Z) in the apparatus coordinate system. Further, in the formula (1), the scalar component $\lambda$ is an arbitrary real number and the projection matrix p is indicated by a matrix consisting of 3 rows and 4 columns.

In X-ray imaging, X-rays which have been outputted from the X-ray generators 41a and 41b and have attenuated by passing through the patient 31 or the calibration object are projected on the flat detection planes of the respective X-ray receivers 42a and 42b (i.e., FPD: Flat Panel Detector). The detection elements corresponding to respective pixels of an originally generated projection image are two-dimensionally arrayed on the flat detection plane of each of the X-ray receivers 42a and 42b.

The first projection image 11 of the calibration object and the second projection image 12 of the patient 31 can be acquired by transforming energy intensity values detected by the respective detection elements two-dimensionally arrayed on the X-ray receiver 42 into luminance values of pixels which positionally correspond to the respective detection elements.

Energy $P_i$ of X-rays which are radiated from the X-ray generator 41 and reach the position $i \in R^2$ of the detection elements on the flat panel of the X-ray receiver 42 can be indicated by the formula (2) in FIG. 2.

In the formula (2), $P_0$ is energy of X-rays immediately after being radiated from the X-ray generator 41 and $\mu(1, P)$ is a linear attenuation coefficient $\mu$ of the patient 31 or the calibration object at the position 1. Note that the linear attenuation coefficient $\mu$ is a value which changes depending on energy P of X-rays penetrating the calibration object or the patient 31.

According to the formula (2), the value obtained by performing line integral on a linear attenuation coefficient of each substance on the path of X-rays from the X-ray generator 41 to the position i of one specified detection element of the X-ray receiver 42 becomes energy of X-rays detected at the position i of this detection element.

A luminance value of each pixel of the first and second projection images 11 and 12 obtained by X-ray imaging is determined according to a sum of products of substances (e.g., the patient) on the path of X-rays which are outputted from the X-ray generators 41a and 41b and reach the detecting element positionally corresponding to this pixel in the X-ray receiver 42a or 42b.

The second projection image 12 (I(u, v)) of the patient 31 imaged by the X-ray imaging structure 40 is geometrically transformed into the transformed projection image 26 (I'(u', v')) by using the transformation parameters 19 and the formula (3) in FIG. 2. Then, maps $f_x$ and $f_y$ indicated by the formula (4) in FIG. 2 are determined, and the relationship indicated by the formula (5) in FIG. 2 is obtained from the projection matrixes p and p'.

Moreover, the relationship indicated by the formula (6) in FIG. 2 is obtained from the simultaneous equations of the formula (5) in FIG. 2. In the formula (6), $H(\lambda)$ is a matrix consisting of 3 rows and 3 columns including each scalar component $\lambda$, and is equivalent to the transformation parameters 19.

The projection matrix p of selected conditions of the X-ray imaging structure 40 is determined by calibration with the use of the calibration object. Since the projection matrix p consisting of 3 rows and 4 columns in the formula (1) includes indefiniteness of constant multiplication $\lambda$, eleven elements are determined. When (u, v) and (X, Y, Z) are known in the formula (1), two equations of constraint about the eleven elements to be determined are obtained. In other words, if there is an object by which at least six (u, v) and (X, Y, Z) can be determined, the projection matrix p can be uniquely determined.

Thus, the projection matrix p can be uniquely determined by the following two steps. In the first step, the calibration object internally including at least six objects whose three-dimensional positions are known are imaged. For instance, metal markers may be used for the at least six objects inside the calibration object. Then, the projection matrix p is determined by specifying coordinates (u, v) of each of the at least six objects inside the calibration object on the image obtained in the first step in association with the known three-dimensional positions (X, Y, Z) of the at least six objects.

Additionally, p' is a design condition and is assumed to be obtained in advance.

Next, the formula (6) will be described in detail with reference to FIG. 3.

Figure 3:
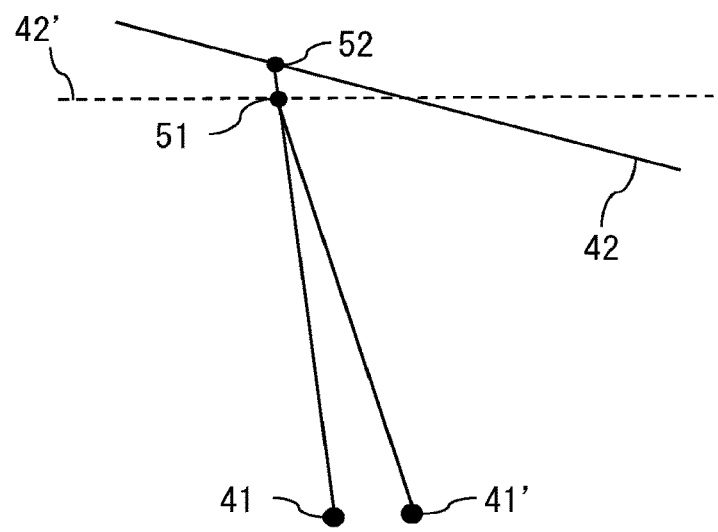
FIG. 3 is a schematic diagram illustrating the principle of deriving transformation parameters.

The reference signs 41' and 42' in FIG. 3 respectively indicate a position of the X-ray generator 41 and a detection plane of the X-ray receiver 42 in the apparatus coordinate system determined on the basis of the design information 13. Similarly, the reference signs 41 and 42 in FIG. 3 respectively indicate a position of the X-ray generator 41 and a detection plane of the X-ray receiver 42 in the apparatus coordinate system determined on the basis of the selected conditions of the X-ray imaging structure 40 in a real space. Note that the detection plane of the X-ray receiver 42 is indicated by straight lines 42 and 42', and the depth of the X-ray receiver 42 is not illustrated in FIG. 3 for avoiding complication. The intersection point between the detection plane of the X-ray receiver 42 and the extended line of the straight line connecting a target point 51 with the reference sign 41 is defined as a reference point 52.

The target point 51 is the position $(u'_d, v'_d)$ of a detection element on the second projection image 12 to be image by the X-ray receiver 42'. Here, it is assumed that the target point 51 in the apparatus coordinate system is the same point as an intersection point whose coordinates are $(X_d, Y_d, Z_d)$ in the apparatus coordinate system. The position $(u_d, v_d)$ of the detection element located at the reference point 52 of the X-ray receiver 42 on the projection image to be imaged by this the X-ray receiver 42 can be determined by substituting $(X_d, Y_d, Z_d, 1)$ for the right-hand side of the first equation of the formula (5) in FIG. 2 (i.e., $(X, Y, Z, 1)^T = (X_d, Y_d, Z_d, 1)$). In the above substitution process, $\lambda_d$ can also be determined. Thus, by substituting the determined $\lambda_d$ and position $(u_d, v_d)$ into the formula (6), the position $(u'_d, v'_d)$ of the detection element located at the target point 51 of the X-ray receiver 42' on the projection image to be imaged by the X-ray receiver 42' can be determined on the basis of the formula (7) in FIG. 2.

When one point in the apparatus coordinate system is extracted, the image coordinates on the detection planes of the respective X-ray receivers 42 and 42', on which X-rays outputted from the X-ray generator 41 are made incident passing through the extracted point, are determined. When the image coordinates of the above two points are determined, the pixel I' (u', v') of the transformed projection image 26 can be determined on the basis of the formula (3).

Thus, by setting the intersection point at the position of each detection element on the X-ray receiver 42', each pixel I' (U', v') of the transformed projection image 26 can be generated. Note that setting of the intersection point is not limited to a position on the X-ray receiver 42 or 42'.

A desirable case of setting method of the intersection point will be described with reference to FIG. 4 drawn by notation similar to FIG. 3.

Figure 4:
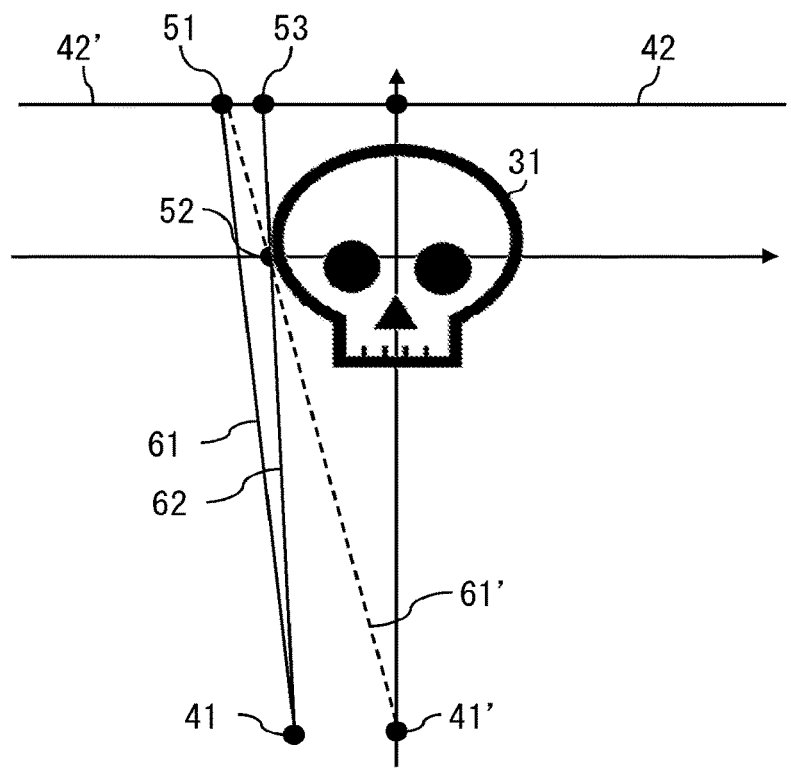
FIG. 4 is another schematic diagram illustrating the principle of deriving transformation parameters.

The reference sign 41' in FIG. 4 indicates a position of the X-ray generator 41 in the apparatus coordinate system determined on the basis of the design information 13. The reference sign 41 in FIG. 4 indicates a position of the X-ray generator 41 in the apparatus coordinate system determined on the basis of the selected conditions of the X-ray imaging structure 40 in a real space. Note that the detection plane of the X-ray receiver 42 is indicated by the straight lines 42 and 42', and the depth of the X-ray receiver 42 is not illustrated in FIG. 3 for avoiding complication.

Although FIG. 4 illustrates a case where the detection plane of the X-ray receiver 42 based on the selected conditions of the X-ray imaging structure 40 in a real space positionally matches the detection plane of the X-ray receiver 42' based on the design information 13 of the X-ray imaging structure 40, even if both do not match each other, the same theory as described below can be applied.

First, the pixel I' (U', v') of the transformed projection image 26 whose position corresponds to the detection element at the target point 51 is determined.

When the intersection point as one point in the apparatus coordinate system is set to the same position as the target point 51 in a manner similar to the case of FIG. 3, energy of X-rays passing through the straight-line path 61 connecting the X-ray generator 41 with the intersection point 51 is converted into a pixel value of the pixel positionally corresponding to the target point 51. In this case, the reference point becomes the same point as the target point 51 and the straight-line path 61 does not pass through the patient 31.

However, the straight-line path 61' connecting the X-ray generator 41' with the intersection point 51 passes through the patient 31. Thus, energy of X-rays passing through the straight-line path 61' is converted into a pixel value far different from the above-described pixel value corresponding to the straight-line path 61.

Next, consider a case where the intersection point 51 is changed to the intersection point 52. In this case, the pixel value of the pixel positionally corresponding to the detection element at the target point 51 becomes the pixel value of the pixel positionally corresponding to the detection element at the reference point 53 on the detection plane of the X-ray receiver 42.

The pixel value of the pixel positionally corresponding to the detection element at the reference point 53 reflects energy of X-rays passing through the straight-line path 62 connecting the X-ray generator 41 with the intersection point 52. Since the straight-line path 62 passes through the patient 31 like the straight-line path 61, the pixel value of the pixel positionally corresponding to the detection element at the reference point 53 becomes closer to the pixel value of the pixel positionally corresponding to the detection element at the target point 51 than the pixel value of the pixel positionally corresponding to the detection element at the reference point 51.

As described above, it is desirable in terms of imaging that a straight-line path passing through the patient 31 is close to a path based on the design information 13. Thus, the intersection point is set to a position where the patient 31 exists. In the case of putting importance on a position of a treatment target, plural intersection points are set on a plane including a straight line along which the therapeutic beam passes. Additionally or alternatively, a position of each intersection point may be set on the basis of the volume data 17 inside the patient' body acquired by CT imaging.

Since analysis of specified voxels constituting the volume data 17 provides a name or a type of a tissue positioned at those specified voxels, positional matching of a part imaged with higher contrast on a projection image such as a bone tissue is often regarded as important in confirmation of a positioning result. Thus, an intersection point is set to a three-dimensional position where the voxel value can be distinguished from a bone tissue.

Depending on setting of each intersection point, it is not possible to determine respective positions of all the detection elements in the transformed projection image I' and some pixels of the transformed projection image are not generated in some cases. In such cases, a general pixel-interpolation method such as a nearest neighbor method, a bilinear method, and a bicubic method is used for completing all the pixels of the transformed projection image.

The transformed image generator 23 can generate plural transformed projection images 26 by using the matrix $H(\lambda)$ whose elements (i.e., scalar components λ) are plural transformation parameters 19 and are different in value from each other. Then, on the basis of the matching reference image whose matching degree with respect to the reconstructed projection image 20 is the highest, determination as to whether the aiming point of a therapeutic beam 35 matches the position of the diseased part of the patient 31 or not is performed.

Incidentally, the matching reference image used for matching processing between the generated the transformed projection image 26 of the patient 31 and the reconstructed projection image 20 may be displayed in parallel, and the subtraction image between both may be displayed. Additionally, plural transformed projection images 26 may be displayed so that one of the displayed transformed projection images 26 is selected via an input device and matching between the reconstructed projection image 20 and the selected transformed projection image 26 is performed.

Next, the radiotherapy method and the radiotherapy program of the present embodiment will be described according to the step numbers in the flowchart shown in FIG. 5 by referring to FIG. 1 as required.

First, the routine from the steps S11 to S15 is calibration of the X-ray imaging structure 40 using the calibration object to be performed as a daily check of the radiotherapy apparatus.

In the step S11, the calibration object is loaded to a predetermined position on the bed 32.

In the next step S12, the bed driving structure 33 is caused to drive based on the positional information 14 so that the calibration object is automatically moved to a previously determined setting position in the irradiation region 34.

In the next step S13, the X-ray imaging structure 40 performs X-ray imaging on the calibration object so as to generate the first projection image 11 of the calibration object.

In the next step S14, the calculator 22 acquires the first projection image 11 and the ideal projection image 18 of the calibration object. The ideal projection image 18 is generated and stored in advance based on the design information 13 of the X-ray imaging structure 40, the positional information 14 of the calibration object, and the volume data 15 of the calibration object.

In the next step S15, the calculator 22 calculates the transformation parameters 19 by which the first projection image 11 is transformed into the ideal projection image 18, on the basis of the generated first projection image 11 and the ideal projection image 18.

Next, the routine from the steps S21 to S31 is processing relevant to radiotherapy on the patient 31.

First, in the step S21, a fixing member by which the patient 31 is fixed to the bed 32 is made in order to precisely irradiate the diseased part with a therapeutic beam.

In the next step S22, prior to irradiation of a therapeutic beam, CT imaging is performed on the patient 31 in the same posture as the posture at the time of being subjected to irradiation of a therapeutic beam with the fixing member mounted on, and thereby the patient volume data 17 are acquired.

In the next step S23, medical staff members discuss a treatment plan for this patient 31. Specifically, the position of the diseased part is three-dimensionally identified based on the volume data 17 inside the patient's body. Then, main irradiation conditions such as irradiation intensity and an irradiation direction of a therapeutic beam are determined so that normal tissues are subjected to as little irradiation as possible.

In the next step S24, the positional information 16 of the patient 31 in the irradiation region 34 is determined. Since the patient 31 is fixed to the bed 32, control conditions of the bed driving structure 33 are uniquely determined on the basis of the positional information 16 of the patient 31.

Here, at an arbitrary timing prior to the step 30 as described below, i.e., in the step 16, the reconstructed projection image 20 as two-dimensional information can be generated from the patient volume data 17 which is three-dimensional information, on the basis of the positional information 16 of the patient 31 in the irradiation region 34 and the design information 13 of the X-ray imaging structure 40.

From the next step S25, a treatment phase using the radiotherapy apparatus starts.

In the step S25, the patient 31 is fixed to the bed 32 with the fixing member.

In the next step S26, the bed 32 is moved to a predetermined position in the irradiation region 34 based on the positional information 16 of the patient 31.

In the next step S27, the X-ray imaging structure 40 performs X-ray imaging on the patient 31 so as to generate the second projection image 12 of the patient 31.

In the next step S28, the transformed image generator 23 acquires the second projection image 12 and the transformation parameters 19.

In the next step S29, the transformed image generator 23 calculates the transformed projection image 26 of the patient 31 which is a resultant image of transforming the second projection image 12 by using the transformation parameters 19.

In the next step S30, a matching reference image of the reconstructed projection image 20 and the transformed projection image 26 of the patient 31 is generated. Further, whether the reconstructed projection image 20 and the transformed projection image 26 of the patient 31 match each other or not is automatically determined on the basis of automatic pattern matching analysis of those images. Note that instead of the above-described automatic determination, a medical staff member may visually determine whether the reconstructed projection image 20 and the transformed projection image 26 of the patient 31 match each other or not.

If the matching determination result is negative (corresponding to NO in the Step 30), the processing returns to the step S26 and the bed driving structure 33 is caused to drive again so that the flow from the steps S26 to S30 is performed again.

Figure 5:
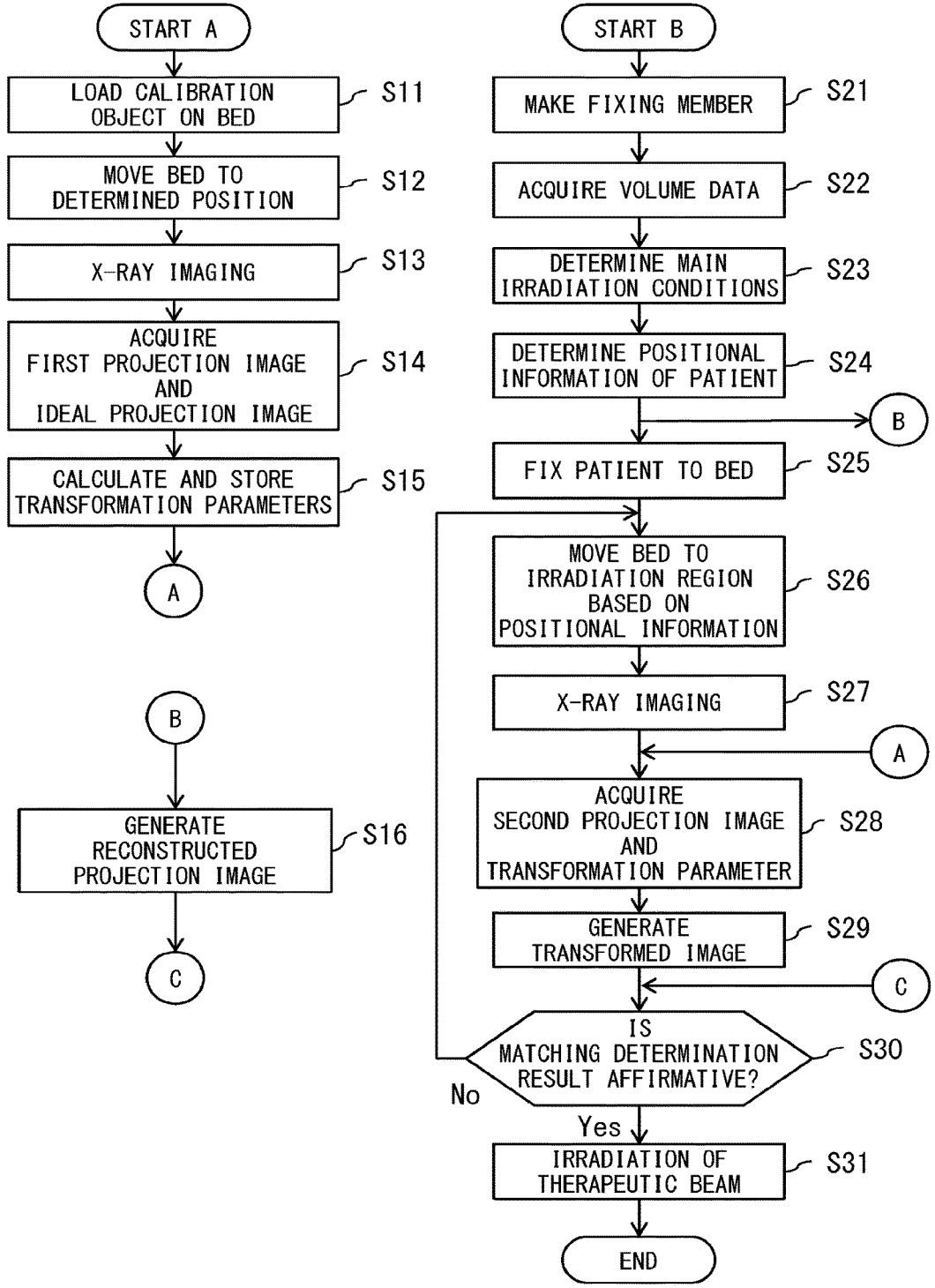
FIG. 5 is a flowchart illustrating a radiotherapy method and a radiotherapy program of the present embodiment.

If the matching determination result is affirmative (corresponding to YES in the Step 30), the processing proceeds to the step S31 in which the therapeutic beam 35 is radiated from the muzzle 36 and the entire processing shown in FIG. 5 is completed.

According to a radiotherapy apparatus of at least one of the above-described embodiments, matching degree between an X-ray projection image of a patient imaged by an X-ray imaging structure and a projection image reconstructed from volume data of the patient is improved with the use of each transformation parameter of a projection image generated by performing X-ray imaging on the calibration object, which enhances accuracy of a therapeutic beam radiated on a diseased part.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The control computer 10 of the radiotherapy apparatus described above includes a control device in which processors such as a special-purpose chip (i.e., integrated circuit), an FPGA (Field Programmable Gate Array), a GPU (Graphics Processing Unit), or a CPU (Central Processing Unit) are integrated, a memory device such as a ROM (Read Only Memory) and a RAM (Random Access Memory), an external memory device such as a HDD (Hard Disk Drive) and an SSD (Solid State Drive), a display device such as a display, an input device such as a mouse and a keyboard, and a communication interface. The control computer 10 can be realized by hardware structure of an ordinary computer.

Programs executed by the control computer 10 of the radiotherapy apparatus are provided by preliminarily installing them in memory circuitry such as a ROM.

Additionally or alternatively, programs executed by the control computer 10 may be provided by storing them in the form of installable or executable electronic files in a memory medium which can be read by a computer. As examples of the above memory medium which can be read by a computer, a CD-ROM, a CD-R, a memory card, a DVD, and a flexible disc are included.

Moreover, programs executed by the control computer 10 of the radiotherapy apparatus of the present embodiment may be stored in a computer connected to a network such as the internet and be provided by being downloaded via the network.

Further, the control computer 10 may be configured by interconnecting separate modules which implement respective functions of the control computer 10 via a network or a dedicated line and combining the interconnected modules.

What is claimed is:

1. A radiotherapy apparatus comprising:
a first receiver configured to receive a first projection image of a calibration object loaded on a bed which has been moved to an irradiation region of a therapeutic beam of treating a patient, the first projection image being obtained under X-ray imaging;
a storing portion configured to store an ideal projection image of the calibration object, the ideal projection image generated based on design information of an X-ray imaging structure which performs the X-ray imaging, positional information of the calibration object in the irradiation region, and volume data of the calibration object;
a calculator configured to calculate at least one transformation parameter by which the first projection image is transformed into the ideal projection image;
a second receiver configured to receive a second projection image obtained by performing the X-ray imaging on the patient lying on the bed which has been moved to the irradiation region;
a transformed image generator configured to generate at least one transformed projection image of the patient which is a resultant image of transforming the second projection image based on the at least one transformation parameter;
a reconstructed image generator configured to generate a reconstructed projection image based on volume data obtained by three-dimensionally imaging inside of a body of the patient, positional information of the patient in the irradiation region, and the design information; and
a matching image generator configured to generate a matching reference image by which matching processing between the transformed projection image and the reconstructed projection image is performed.

2. The radiotherapy apparatus according to claim 1,
wherein the at least one transformation parameter comprises plural transformation parameters;
the plural transformation parameters are indicated by a matrix including scalar components; and
the transformed image generator is configured to generate plural transformed projection images by using the plural transformation parameters which are different in scalar component value from each other.

3. The radiotherapy apparatus according to claim 1, further comprising a beam irradiator configured to radiate the therapeutic beam when the transformed projection image and the reconstructed projection image match each other in the matching processing based on the matching reference image.

4. A radiotherapy method comprising:
receiving a first projection image of a calibration object loaded on a bed which has been moved to an irradiation region of a therapeutic beam of treating a patient, the first projection image being obtained under X-ray imaging;
storing an ideal projection image of the calibration object, the ideal projection image generated based on design information of an X-ray imaging structure which performs the X-ray imaging, positional information of the calibration object in the irradiation region, and volume data of the calibration object;
calculating a transformation parameter by which the first projection image is transformed into the ideal projection image;
receiving a second projection image obtained by performing the X-ray imaging on the patient lying on the bed which has been moved to the irradiation region;
generating a transformed projection image of the patient which is a resultant image of transforming the second projection image based on the transformation parameter;
generating a reconstructed projection image based on the design information, positional information of the patient in the irradiation region, and volume data obtained by three-dimensionally imaging inside of a body of the patient; and
generating a matching reference image by which matching processing between the transformed projection image and the reconstructed projection image is performed.

* * * * *